(12) United States Patent
Ohno

(10) Patent No.: US 11,528,395 B2
(45) Date of Patent: Dec. 13, 2022

(54) CAMERA HEAD

(71) Applicant: Sony Olympus Medical Solutions Inc., Tokyo (JP)

(72) Inventor: Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/937,602

(22) Filed: Jul. 24, 2020

(65) Prior Publication Data
US 2021/0037170 A1 Feb. 4, 2021

(30) Foreign Application Priority Data
Aug. 2, 2019 (JP) .............................. JP2019-143382

(51) Int. Cl.
| | | |
|---|---|---|
| H04N 5/00 | (2011.01) | |
| G02B 23/00 | (2006.01) | |
| H04N 5/225 | (2006.01) | |
| G02B 23/24 | (2006.01) | |

(52) U.S. Cl.
CPC ....... H04N 5/2254 (2013.01); G02B 23/2484 (2013.01); G02B 23/2469 (2013.01)

(58) Field of Classification Search
CPC .... A61B 1/042; A61B 1/128; G02B 23/2469; G02B 23/2484; H04N 2005/2255; H04N 5/2254; H04N 5/2252
See application file for complete search history.

(56) References Cited

U.S. PATENT DOCUMENTS

| | | | | |
|---|---|---|---|---|
| 4,697,894 A | * | 10/1987 | Takamura | .......... G02B 23/2476 359/503 |
| 6,080,101 A | * | 6/2000 | Tatsuno | ............. A61B 1/00124 348/65 |
| 2006/0229495 A1 | * | 10/2006 | Frith | ................... A61B 1/00126 600/112 |
| 2014/0094657 A1 | * | 4/2014 | Miyamoto | ........... A61B 1/0016 600/114 |
| 2016/0100748 A1 | * | 4/2016 | Kohno | ............... A61B 1/00009 348/65 |
| 2018/0035878 A1 | * | 2/2018 | Nara | ....................... G03B 17/55 |
| 2019/0357760 A1 | * | 11/2019 | Nara | ....................... A61B 1/042 |

FOREIGN PATENT DOCUMENTS

| | | | |
|---|---|---|---|
| JP | 6401427 B1 | 10/2018 | |
| WO | WO-2018116533 A1 * | 6/2018 | ......... A61B 1/00188 |

* cited by examiner

*Primary Examiner* — Zhihan Zhou
(74) *Attorney, Agent, or Firm* — Xsensus LLP

(57) ABSTRACT

A camera head includes: a mount detachably connected to an eyepiece of an endoscope; an imager configured to capture a subject image emitted from the eyepiece; and a housing configured to house the imager, the housing including an interior portion including the imager thereinside, and an exterior portion arranged on an outer side of the interior portion, wherein the interior portion and the exterior portion are separated from each other in at least a part of an outer surface.

10 Claims, 5 Drawing Sheets

CAMERA HEAD

This application claims priority from Japanese Application No. 2019-143382, filed on Aug. 2, 2019, the contents of which are incorporated by reference herein in its entirety.

BACKGROUND

The present disclosure relates to a camera head.

In camera heads connected to an endoscope, heat generated by an imaging device housed inside a camera head or the like has been radiated from an exterior that covers an outer surface of the camera head (for example, Japanese Patent No. 6401427). Because exteriors of a camera head are portions held by users, allowable temperature is defined by product standards.

SUMMARY

In recent years, there is an increasing trend in the amount of heat generated in an imaging device or the like originated in increased resolution to improve the image quality, and the like. When the amount of heat generated in the imaging device and the like becomes large, it may exceed the allowable temperature of the exterior.

There is a need for a camera head, an exterior of which is prevented from becoming high temperature.

According to one aspect of the present disclosure, there is provided a camera head including: a mount detachably connected to an eyepiece of an endoscope; an imager configured to capture a subject image emitted from the eyepiece; and a housing configured to house the imager, the housing including an interior portion including the imager thereinside, and an exterior portion arranged on an outer side of the interior portion, wherein the interior portion and the exterior portion are separated from each other in at least a part of an outer surface.

DETAILED DESCRIPTION

Hereinafter, forms to implement the present disclosure (hereinafter, embodiments) will be described with reference to the drawings. Embodiments described below are not intended to limit the present disclosure. Moreover, identical reference symbols are assigned to identical components throughout the drawings.

Configuration of Endoscope Device

Figure 1:
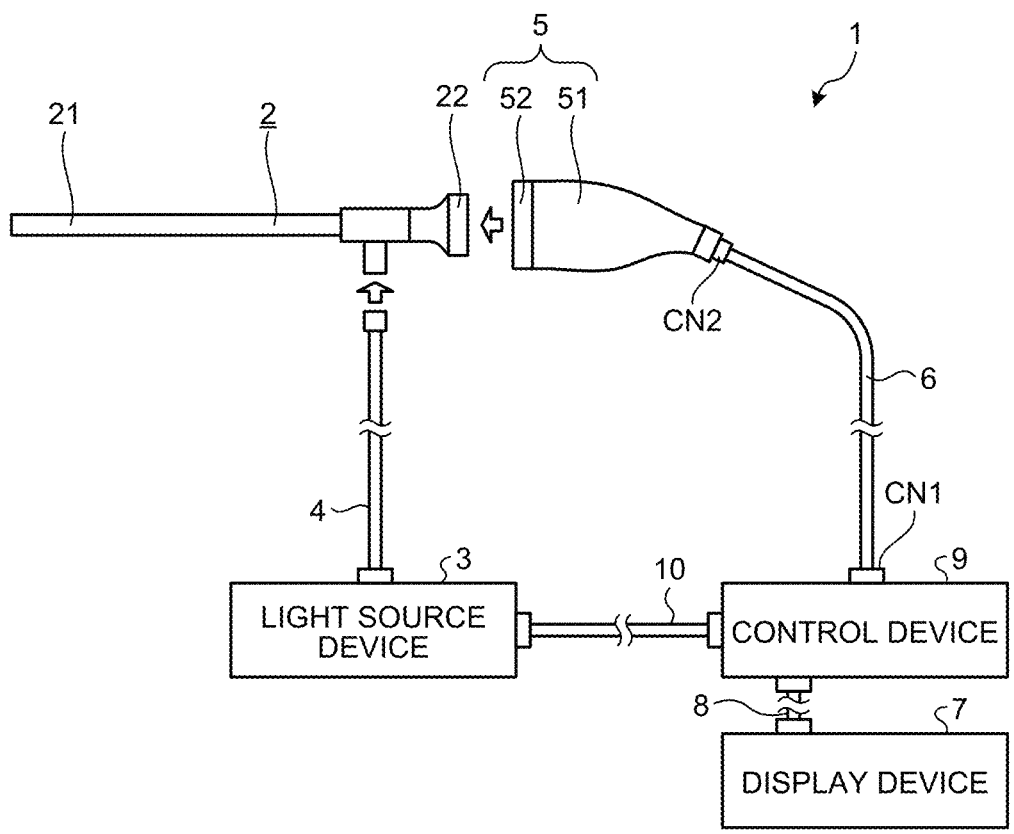
FIG. 1 illustrates a schematic configuration of an endoscope device that includes a camera head according to an embodiment.

FIG. 1 illustrates a schematic configuration of an endoscope device that includes a camera head according to an embodiment. An endoscope device 1 is a device that is used in a medical field to observe the inside of a living body. This endoscope device 1 includes, as illustrated in FIG. 1, an endoscope 2, a light source device 3, a light guide 4, a camera head 5, a first transmission cable 6, a display device 7, a second transmission cable 8, a control device 9, and a third transmission cable 10.

The endoscope 2 is constituted of a rigid endoscope. That is, the endoscope 2 has a long and thin shape, the entirety of which is rigid, or a part of which is flexible and the other part of which is rigid, and is inserted into a living body. This endoscope 2 includes, as illustrated in FIG. 1, an insertion portion 21 and an eyepiece portion 22.

The insertion portion 21 is a portion that extends straight, and that is inserted into a living body. This insertion portion 21 includes an optical system (not illustrated) that is constituted of one or more pieces of lenses, and that condenses a subject image.

The eyepiece portion 22 is arranged at a proximal end (right end portion in FIG. 1) of the insertion portion 21. In this eyepiece portion 22, an eyepiece optical system (not illustrated) that emits the subject image condensed by the optical system (not illustrated) in the insertion portion 21 from the eyepiece portion 22 is arranged. The eyepiece portion 22 has a diameter that increases toward a proximal end.

The light source device 3 is connected to one end of the light guide 4, and provides light to illuminate the inside of a living body to one end of the light guide 4 under control of the control device 9.

The one end of the light guide 4 is detachably connected to the light source device 3, and the other end is detachably connected to the endoscope 2. The light guide 4 transmits light provided by the light source device 3 from one end to the other end, to provide to the endoscope 2. The light provided to the endoscope 2 is emitted from a distal end (left end portion in FIG. 1) of the endoscope 2, and illuminated to the inside of the living body. The light illuminated to the inside of the living body and then reflected on the inside of the living body (subject image) is collected by the optical system (not illustrated) in the insertion portion 21.

The camera head 5 includes a housing unit 51 that houses thereinside an imaging device 512 described later, and the like, and a mounting unit 52 that is detachably connected to the eyepiece portion 22 of the endoscope 2. In the camera head 5, the imaging device 512 captures the subject image emitted from the eyepiece portion 22, and outputs an image signal (RAW signal) obtained by the imaging, under control of the control device 9. The image signal is, for example, an image signal equal to or higher than 4K resolution. Detailed forms of the housing unit 51 and the mounting unit 52 are described later.

One end of the first transmission cable 6 is detachably connected to the control device 9 through a connector CN1, and the other end is detachably connected to the camera head 5 through a connector CN2. The first transmission cable 6 transmits the image signal and the like output from the camera head 5 to the control device 9, and respectively transmits a control signal, a synchronization signal, a clock, an electric power, and the like output from the control device 9 to the camera head 5.

The transmission of the image signal and the like from the camera head 5 to the control device 9 through the first transmission cable 6 may be performed by transmitting the image signal and the like by an optical signal, or by an electrical signal. The same applies to the transmission of the control signal, the synchronization signal, and the clock from the control device 9 to the camera head 5 through the first transmission cable 6.

The display device 7 is constituted of a display using a liquid crystal, an organic electroluminescence (EL), and the like, and displays a captured image based on a video signal from the control device 9, under control of the control device 9.

One end of the second transmission cable 8 is detachably connected to the display device 7, and the other end is detachably connected to the control device 9. The second transmission cable 8 transmits the video signal processed by the control device 9 to the display device 7.

The control device 9 includes a central processing unit (CPU) and the like, and controls operation of the light source device 3, the camera head 5, and the display device 7 in a centralized manner.

For example, the control device 9 generates a video signal by subjecting an image signal acquired from the camera head 5 through the first transmission cable 6 to various kinds of processing, and outputs the video signal to the display device 7 through the second transmission cable 8. The display device 7 displays the captured image based on the video signal. Moreover, the control device 9 outputs a control signal and the like to the camera head 5 and the light source device 3 through the first and the third transmission cable 6, 10.

One end of the third transmission cable 10 is detachably connected to the light source device 3, and the other end is detachably connected to the control device 9. The third transmission cable 10 transmits a control signal from the control device 9 to the light source device 3.

Configuration of Camera Head

Figure 2:
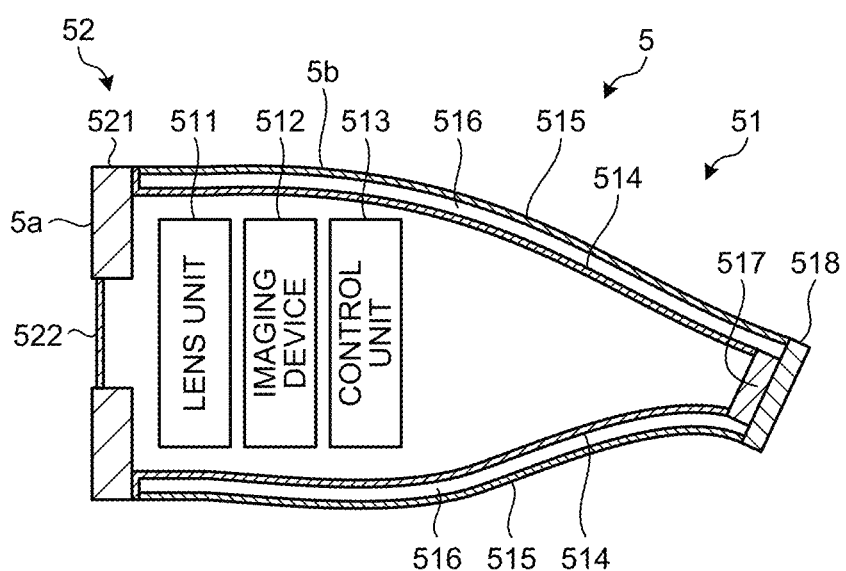
FIG. 2 illustrates a schematic configuration of the camera head illustrated in FIG. 1.

FIG. 2 illustrates a schematic configuration of the camera head illustrated in FIG. 1. As illustrated in FIG. 2, the camera head 5 includes the housing unit 51 and the mounting unit 52.

The housing unit 51 includes a lens unit 511, an imaging device 512, a control unit 513, an interior portion 514, an exterior portion 515, a heat insulating layer 516, a first connector portion 517, and a second connector portion 518.

The lens unit 511 forms an image of the subject image condensed by the insertion portion 21 and entering through the optical device 522 on an imaging surface.

The imaging device 512 images the inside of a living body, under control of the control device 9. This imaging device 512 includes a charge coupled device (CCD), a complementary metal oxide semiconductor (CMOS), or the like that receives the subject image that is condensed by the insertion portion 21, and that is formed by the lens unit 511 through the optical device 522, to convert into an electrical signal.

The control unit 513 includes a CPU or the like, and controls operation of the endoscope device 1 including the camera head 5 in a centralized manner, according to a user operation, a control signal from the control device 9, and the like.

The interior portion 514 has the imaging device 512 thereinside. The interior portion 514 is made from a metal, an alloy, or the like.

The exterior portion 515 is arranged outside the interior portion 514. The exterior portion 515 is formed from a metal, an alloy, or the like. The exterior portion 515 may be formed from a material identical to the interior portion 514, or from a different material.

The heat insulating layer 516 is arranged between the interior portion 514 and the exterior portion 515, and is made from a material having a thermal conductivity lower than the inside of the interior portion 514. The heat insulating layer 516 may be, for example, a vacuum layer, and may also be a layer filled with gas such as Ar gas, air, or a heat insulating material.

The first connector portion 517 is a hermetic connector, and the inside of the camera head 5 is air-tightly sealed with the first connector portion 517.

The second connector portion 518 is a receptacle connector, and the connector CN2 of the first transmission cable 6 is connected thereto.

The mounting unit 52 includes a connecting portion 521 and an optical device 522.

The connecting portion 521 is formed in, for example, a ring shape, and connects the eyepiece portion 22 and the mounting unit 52.

The optical device 522 is fixed in the connecting portion 521, for example, by solder, and seals an opening of the camera head 5 on a distal end side in an air-tight manner. This optical device 522 is constituted of, for example, a planer sapphire glass.

Heat Radiation Structure of Camera Head

An outer surface of the housing unit 51 includes an abutting surface 5$a$ that abuts on the eyepiece portion 22, and a side surface 5$b$ that continues to the abutting surface 5$a$. The interior portion 514 and the exterior portion 515 are separated from each other on the side surface 5$b$. Between the interior portion 514 and the exterior portion 515, the vacuum heat insulating layer 516 is arranged, and transmission of heat generated by the imaging device 512 positioned inside the camera head 5 and the like to the exterior portion 515 is prevented thereby. As a result, according to the embodiment, the exterior portion 515 is prevented from becoming high temperature. The abutting surface 5$a$ is not a portion that is touched by a user when the user holds the camera head 5 because it abuts on the eyepiece portion 22 and, therefore, is a portion not needed to be prevented from becoming high temperature.

Moreover, a contact area between the interior portion 514 and the exterior portion 515 is smaller than a contact area between the interior portion 514 and the mounting unit 52. As a result, an amount of heat transmitted from the interior portion 514 to the mounting unit 52 is larger than an amount of heat transmitted from the interior portion 514 to the exterior portion 515, and a structure in which heat inside the camera head 5 is radiated toward a distal end side (direction of the eyepiece 22) through the mounting unit 52 is obtained. By radiating heat inside the camera head 5 toward the distal end side, it is possible to prevent the imaging device 512, the control unit 513, and the like from becoming high temperature.

In the embodiment described above, a structure in which the interior portion 514 and the exterior portion 515 is separated by the side surface 5$b$ out of the outer surface of the camera head 5 has been explained as an example, but it is only necessary that the interior portion 514 and the exterior portion 515 are separated at least at a part of the outer surface of the camera head 5. Particularly, it is preferable that the interior portion 514 and the exterior portion 515 be separated in an entire portion that is touched by a user when the user holds the camera head 5, out of the outer surface of the camera head 5.

Figure 3:
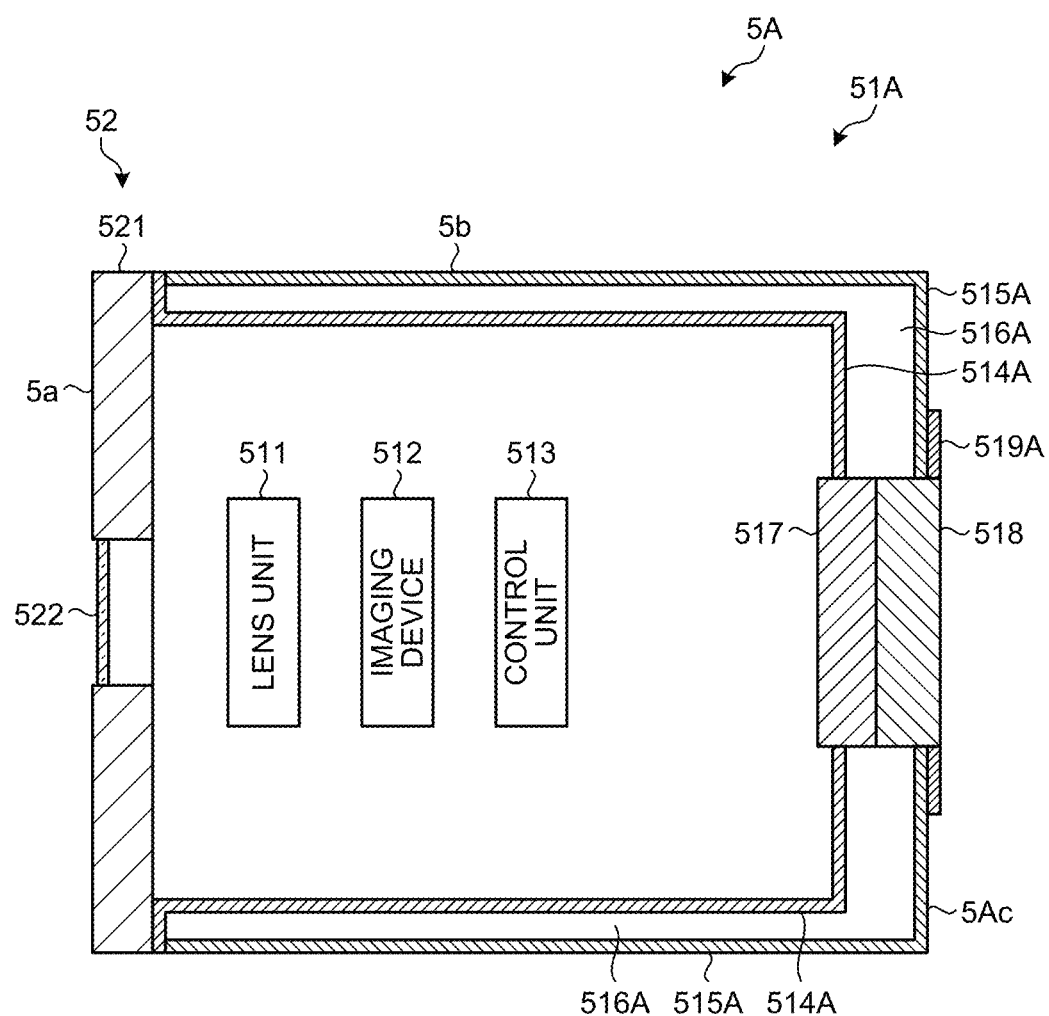
FIG. 3 illustrates a schematic configuration of a camera head according to a first modification.

FIG. 3 illustrates a schematic configuration of a camera head according to a first modification. As illustrated in FIG. 3, a camera head 5A has a cylindrical housing unit 51A in which an interior portion 514A and an exterior portion 515A are separated from each other on a side surface 5$b$ and a rear surface 5Ac. Between the interior portion 514A and the exterior portion 515A, a heat insulating layer 516A is arranged. In this camera head 5A, the second connector portion 518 and a cover portion 519A abut on the connector CN2. As a result, a part of the side surface 5b and the rear surface 5Ac is insulated by the heat insulating layer 516 because it is a portion touched by a user when the user holds the camera head 5A.

As the first modification, when there is a portion touched by a user when the user hold the camera head 5 also on a rear surface and the like besides a side surface, it is preferable that the interior portion 514 and the exterior portion 515 be separated from each other in an entire portion to be touched.

Figure 4:
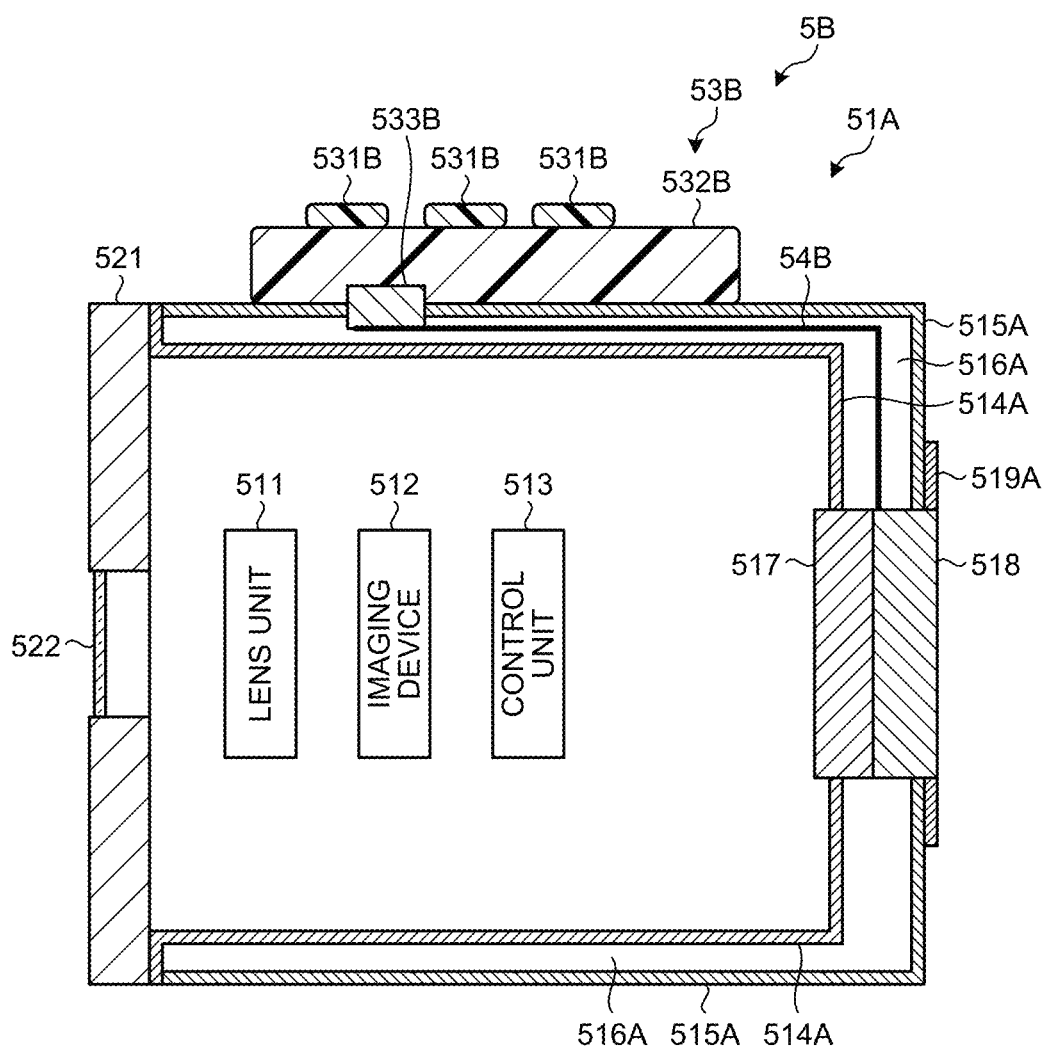
FIG. 4 illustrates a schematic configuration of a camera head according to a second modification.

FIG. 4 illustrates a schematic configuration of a camera head according to a second modification. As illustrated in FIG. 4, a camera head 5B includes a switch portion 53B and a flexible board 54B.

The switch portion 53B is arranged on an outer side of the exterior portion 515A, and includes an operation button 531B that receives an operation input with respect to the camera head 5, a button frame 532B that is attached to the operation button 531B, and a switch connector portion 533B that electrically connects the operation button 531B and the flexible board 54B.

The switch connector portion 533B is a hermetic connector, and air-tightly seals the inside of the camera head 5.

The flexible board 54B electrically connects the control unit 513 and the switch portion 53B through the first connector portion 517 and the second connector portion 518. The flexible board 54B is arranged between the interior portion 514A and the exterior portion 515A.

According to the second modification, by arranging the flexible board 54B between the interior portion 514A and the exterior portion 515A, space between the interior portion 514A and the exterior portion 515A may be used efficiently.

Figure 5:
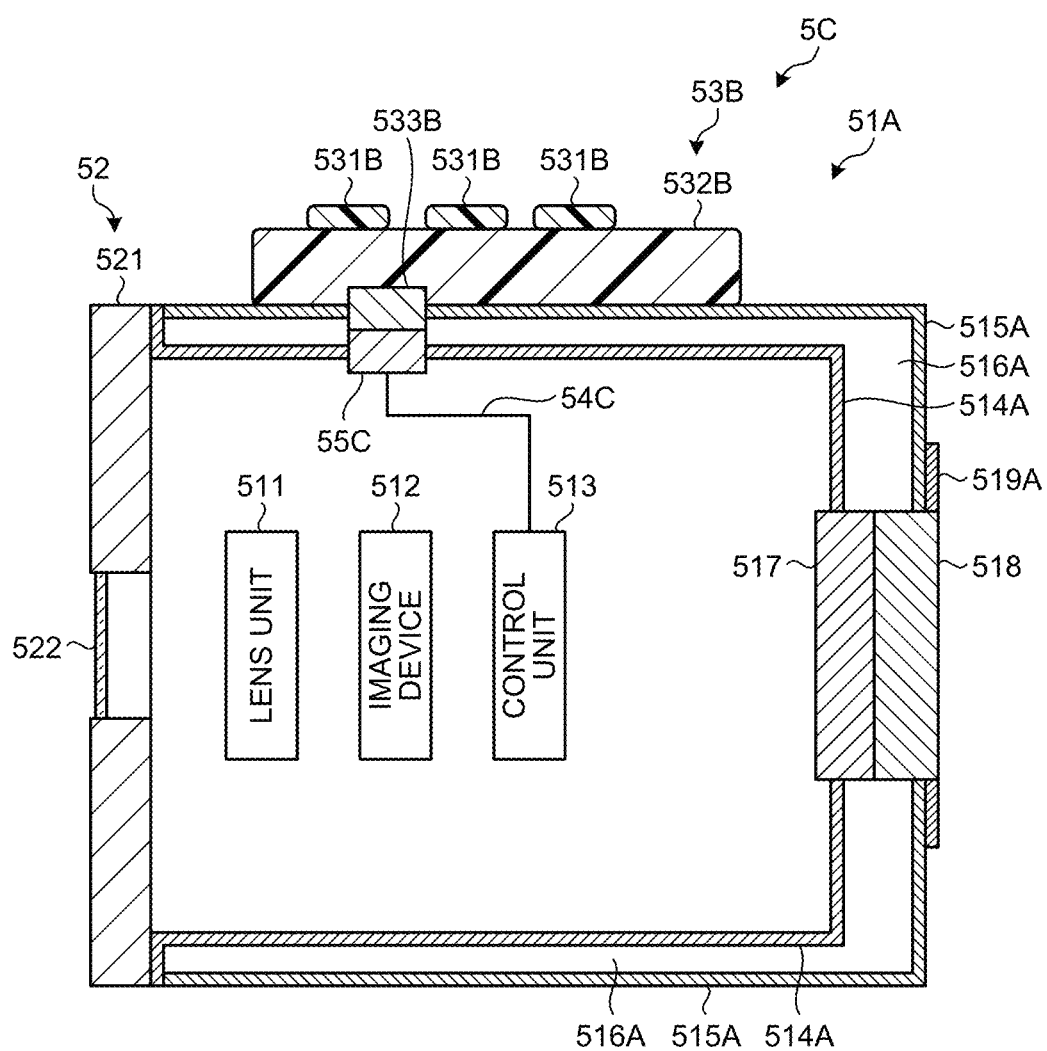
FIG. 5 illustrates a schematic configuration of a camera head according to a third modification.

FIG. 5 illustrates a schematic configuration of a camera head according to a third modification. As illustrated in FIG. 5, a camera head 5C includes a flexible board 54C and an interior-side connector portion 55C.

The flexible board 54C electrically connects the control unit 513 and the switch portion 53B directly.

The interior-side connector portion 55C electrically connects the switch connector portion 533B and the flexible board 54C. The interior-side connector portion 55C is a hermetic connector, and air-tightly seals the inside of the camera head 5.

As the third modification, the control unit 513 and the switch portion 53B may be electrically connected by the flexible board 54C directly.

Figure 6:
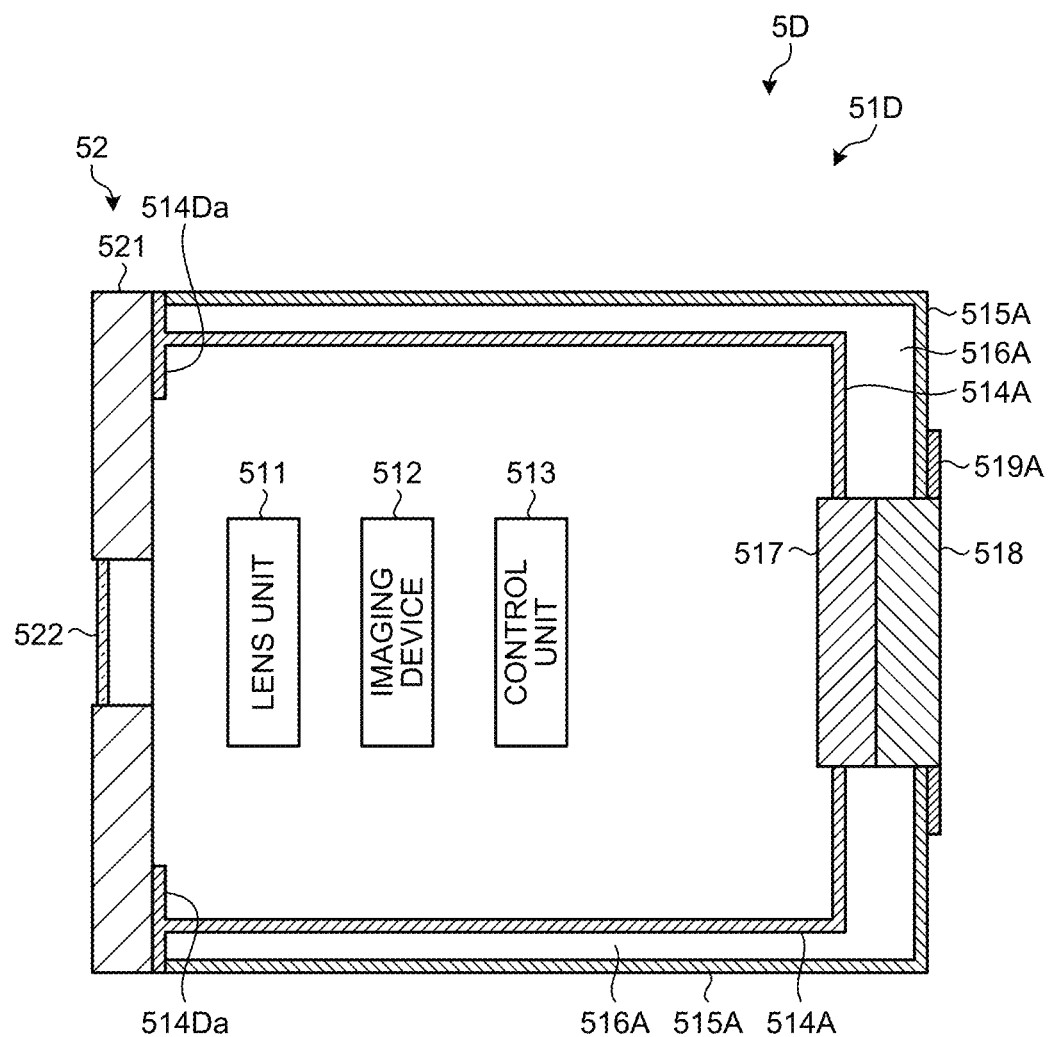
FIG. 6 illustrates a schematic configuration of a camera head according to a fourth modification.

FIG. 6 illustrates a schematic configuration of a camera head according to a fourth modification. As illustrated in FIG. 6, in a camera head 5D, an interior portion 514D of a housing unit 51D includes a flange portion 514Da.

Because the flange portion 514Da contributes to increase a contact area between the interior portion 514D and the mounting unit 52, heat transmitted from the interior portion 514D to the mounting unit 52 increases. As a result, heat inside the camera head 5D may be effectively radiated toward a distal end side, and the effect that the exterior portion 515 is prevented from becoming high temperature may be enhanced.

According to the present disclosure, a camera head, an exterior of which is prevented from becoming high temperature may be provided.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head comprising:
    an imager configured to capture a subject image emitted from an eyepiece of an endoscope; and
    a housing configured to house the imager, the housing including
        an interior portion including the imager thereinside,
        an exterior portion arranged on an outer side of the interior portion, and
        a heat insulating layer having a thermal conductivity lower than inside of the interior portion between the interior portion and the exterior portion where they are separated from each other.

2. The camera head according to claim 1, wherein
    the housing includes an abutting surface configured to abut a mount detachably connected to the eyepiece and a side surface that continues to the abutting surface, and
    the interior portion and the exterior portion are separated from each other on the side surface.

3. The camera head according to claim 2, wherein a contact area between the interior portion and the exterior portion is smaller than a contact area between the interior portion and the mount.

4. The camera head according to claim 1, wherein a contact area between the interior portion and the exterior portion is smaller than a contact area between the interior portion and a mount detachably connected to the eyepiece.

5. The camera head according to claim 4, further comprising:
    a controller configured to control operation of the camera head;
    a switch arranged on an outer side of the exterior portion, the switch including an operation button receiving an operation input with respect to the camera head; and
    a flexible board configured to connect the controller and the switch electrically.

6. The camera head according to claim 5, wherein the flexible board is arranged between the interior portion and the exterior portion.

7. The camera head according to claim 1, further comprising:
    a controller configured to control operation of the camera head;
    a switch arranged on an outer side of the exterior portion, the switch including an operation button receiving an operation input with respect to the camera head; and
    a flexible board configured to connect the controller and the switch electrically.

8. The camera head according to claim 7, wherein the flexible board is arranged between the interior portion and the exterior portion.

9. The camera head according to claim 1, further comprising:
    a connector that includes an abutting surface configured to abut the eyepiece, wherein the connector is separate from the interior portion and the exterior portion and contacts at least one of the interior portion and the exterior portion.

10. The camera head according to claim 9, wherein a contact area between the interior portion and the exterior portion is smaller than a contact area between the interior portion and the connector.

* * * * *